United States Patent
Drent et al.

(10) Patent No.: US 6,835,850 B2
(45) Date of Patent: Dec. 28, 2004

(54) PROCESS FOR THE CARBONYLATION OF A CONJUGATED DIENE

(75) Inventors: Eit Drent, Amsterdam (NL); Willem Wabe Jager, Amsterdam (NL); Otto Erik Sielcken, Sittard (NL); Imre Toth, Geleen (NL)

(73) Assignee: DSW IP Assets B.V., Heerlen (NL)

( * ) Notice: Subject to any disclaimer, the term of this patent is extended or adjusted under 35 U.S.C. 154(b) by 4 days.

(21) Appl. No.: 10/381,040

(22) PCT Filed: Sep. 26, 2001

(86) PCT No.: PCT/NL01/00709
§ 371 (c)(1),
(2), (4) Date: Aug. 25, 2003

(87) PCT Pub. No.: WO02/26690
PCT Pub. Date: Apr. 4, 2002

(65) Prior Publication Data
US 2004/0039226 A1 Feb. 26, 2004

(30) Foreign Application Priority Data
Sep. 27, 2000 (EP) .............................. 00203355
Sep. 27, 2000 (EP) .............................. 00203356

(51) Int. Cl.$^7$ ............................................. C07C 67/36
(52) U.S. Cl. ........................ 560/207; 562/522; 502/155
(58) Field of Search ........................ 560/207; 562/522; 502/155

(56) References Cited

U.S. PATENT DOCUMENTS 4,172,087 A * 10/1979 Knifton
4,414,409 A * 11/1983 Walker
5,495,041 A * 2/1996 Sielcken et al.

FOREIGN PATENT DOCUMENTS

| EP | 0918521 | * 10/1986 |
| EP | 273489 | 7/1991 |
| EP | 284170 | 10/1991 |
| EP | 577204 | 10/1996 |
| WO | WO 97/33854 | * 9/1997 |
| WO | WO 98/35938 | * 8/1998 |
| WO | 00/56695 | 9/2000 |

* cited by examiner

Primary Examiner—Paul J. Killos
(74) Attorney, Agent, or Firm—Mayer, Brown, Rowe & Haw LLP

(57) ABSTRACT

Process for the carbonylation of a conjugated diene by reacting the conjugated diene with carbon monoxide and an hydroxyl group containing compound in the presence of a catalyst system based on: (a) a source of palladium cations, (b) a diphosphine ligand, and (c) a source of anions, wherein the diphosphine ligand is a ligand having the general formula I wherein $x^1$ and $x^2$ represent a cyclic group with at least 5 ring atoms, of which one is a phosphorus atom, and R represents a bivalent aliphatic bridging group, connecting both phosphorus atoms, containing from 2 to 4 atoms in the bridge, which is substituted with at least one substituent or R represents a phenyl group with both phosphorus groups bound to the 1,2-position.

16 Claims, No Drawings

PROCESS FOR THE CARBONYLATION OF A CONJUGATED DIENE

CROSS REFERENCE TO RELATED APPLICATION

This application is the National Phase of International Application PCT/NL01/00709 filed Sep. 26, 2001 which designated the U.S., which claims priority to European application 00203356.1, filed Sep. 27, 2000 and application 00203355.3, filed Sep. 27, 2000.

The invention relates to a process for the carbonylation of a conjugated diene by reacting the conjugated diene with carbon monoxide and an hydroxyl group containing compound in the presence of a catalyst system comprising (a) a source of palladium cations, (b) a diphosphine ligand, and (c) a source of anions. In particular it relates to the preparation of alkyl pentenoates and/or adipates from 1,3-butadiene and derivatives thereof.

A carbonylation reaction means every reaction between a non-saturated substrate, an hydroxyl group containing compound and carbon monoxide.

U.S. Pat. No. 5,495,041 describes a process for the preparation of a pentenoate ester by carbonylation of butadiene in the presence of carbon monoxide, alcohol and a catalyst system comprising palladium, pentenoic acid and a phosphine ligand. The phosphine ligand can be a monodentate or multidentate phosphine ligand or a mixture thereof. As possible bidentate phosphine ligands 2,3-dimethyl-1,4-bis(diphenylphospino)butane, 2,3-bis(diphenylphospino)-2-butene, 1,3 bis(diphenylphosphino)-2-oxopropane and 1,2-bis(diphenylphosphino)cyclohexane are mentioned. A disadvantage of the process as described in U.S. Pat. No. 5,495,041 is that the catalyst system has only a moderate activity.

An object of the present invention is to provide an improved process in terms of catalyst activity for carbonylation of conjugated dienes.

This object is achieved in that the diphosphine ligand is a ligand having the general formula I

$$X^1\text{---}R\text{---}X^2 \qquad (I)$$

wherein $X^1$ and $X^2$ represent a cyclic group with at least 5 ring atoms, of which one is a phosphorus atom, and R represents a bivalent aliphatic bridging group, connecting both phosphorus atoms, containing from 2 to 4 atoms in the bridge, which is substituted with at least one substituent or R represents a phenyl group with both phosphorus groups bound to the 1,2-position.

It has surprisingly been found that when such a process is carried out with such a specific choice of diphosphine ligand unexpected advantages with regard to the catalyst activity are obtained.

Another advantage is that the catalyst system remains stable over a prolonged period of time and can be reused several times without loss or without substantial loss of catalyst activity.

WO-A-0056695 describes a process for the preparation of mono- and diesters by reaction of a conjugated diene, with carbon monoxide and an hydroxyl group containing compound in the presence of a catalyst system including a source of palladium cations, a diphosphine ligand and a source of anions. As a possible diphosphine ligand 1,2-P,P'-bis(9-phosphabicyclononyl)propane is mentioned. Although acceptable catalyst activity is obtained, there is still room for further improvement. Also this known catalyst system leaves room for improvement regarding stability. The process of the present invention is specifically directed to the carbonylation of conjugated dienes, which show specific reaction characteristics when compared to ethylenically unsaturated compounds in general. Conjugated dienes contain at least two conjugated double bonds in the molecule. By conjugation is meant that the location of the π-orbital is such that it can overlap other orbitals in the molecule. Thus, the effects of compounds with at least two conjugated double bonds are often different in several ways from those of ethylenically unsaturated compounds with no conjugated double bonds. It is generally acknowledged that the carbonylation of conjugated dienes comprises more difficulties than that of an ethylenically unsaturated compound with no conjugated double bonds. In contrast to ethylenically unsaturated compounds with no conjugated double bonds, carbonylation of conjugated dienes involves Pd-π-allyl intermediate species, which are relatively stable against carbonmonoxide insertion reactions.

The bridging group R of the diphosphine ligand represents a bivalent aliphatic bridging group, connecting both phosphorus atoms, containing from 2 to 4 atoms in the bridge, which is substituted with at least one substituent or R represents a phenyl group, with both phosphorus groups bound to the 1,2-position.

Preferably the bridging group R represents a bivalent aliphatic bridging group, connecting both phosphorus atoms, containing from 2 to 4 atoms in the bridge, which is substituted with at least one substituent.

By "a bridge" is understood the shortest connection between both phosphorus atoms. Preferably, the bridging group R represents an alkylene group containing from 2 to 4 carbons atoms in the bridge, but it can also comprise a carbon chain, interrupted by a hetero atom, such as nitrogen, sulphur, silicon or oxygen atom. Preferably the bridge is a substituted alkylene group with at least one substituent and more preferably at least two substituents. Preferably the alkylene group is substituted with two to four substituents and more preferably with two to three substituents. Most preferably the alkylene group is substituted with two substituents. More preferably the bridging group R is a substituted dimethylene or trimethylene group, most preferably a substituted dimethylene group.

The substituents can be attached to any part of the bridge. In an advantageous embodiment, the carbon atoms of the bridge, which are connected to the phosphorus atoms, are substituted. In this case, the bidentate ligand has two chiral C-atoms and can have the R,R, SS, or R,S meso form. From a technical point of view, based on its greater activity, the R,S meso form is preferred. From a commercial point of view, a mixture of the possible stereochemical configurations of the bidentate ligand is preferred because this mixture is the most easy to prepare and such a mixture is inherently formed under the applied reaction conditions of the process of the invention. In another advantageous embodiment the substitution is vicinal.

The substituents can contain carbon atoms and/or hetero atoms, such as halides, sulphur, phosphor, oxygen and nitrogen. Preferably the substituents are hydrocarbyl groups. The hydrocarbyl groups itself can be aromatic, aliphatic or cycloaliphatic and can contain carbon atoms and hetero atoms. The hydrocarbyl groups include straight-chain or branched saturated or non-saturated carbon containing groups.

Preferred hydrocarbyl groups are alkyl groups, preferably having from 1 to 10 carbon atoms, more preferably from 1 to 4 carbon atoms. Linear, branched or cyclic alkyl groups can be used. Suitable alkyl groups include, methyl, ethyl, propyl, iso-propyl, butyl and iso-butyl. More suitably methyl groups are used.

Preferably, the bridge is substituted with at least two alkyl groups. Preferably the bridging group is substituted with two to four alkyl groups and more preferably with two to three alkyl groups. Most preferably the bridge is substituted with two alkyl groups.

Preferably the alkyl groups have from 1 to 10 carbon atoms, more preferably from 1 to 4 carbon atoms. Saturated or non-saturated, linear, branched or cyclic alkyl groups can be used. Suitable alkyl groups include, methyl, ethyl, propyl, iso-propyl, butyl, iso-butyl, tert-butyl and cyclopentyl. More preferably methyl groups are used.

Most preferably the bivalent aliphatic bridging group R is an alkylene group which is di-substituted in the bridge with two alkyl groups, most preferably with two methyl groups.

$X^1$ and $X^2$ represent a substituted or non-substituted cyclic group with at least 5 ring atoms, of which one is a phosphorus atom, and preferably with from 6 to 12 ring atoms. The cyclic group can be a monocyclic group, such as for example a phosphacyclohexyl or phosphacyclooctyl group, or a polycyclic group. Preferably the cyclic group(s) is/are a bicyclic group, such as for example a 7-phosphabicycloheptyl, a 8-phosphabicyclooctyl or a 9-phosphabicyclononyl group. Most advantageously both $X^1$ and $X^2$ represent a substituted or non-substituted 9-phosphabicyclononyl group. The 9-phosphabicyclononyl group can have several isomeric structures. For the purpose of the invention the [3,3,1] and [4,2,1] isomers are preferred. Suitably $X^1$ and $X^2$ are substituted or non-substituted [3,3,1] or [4,2,1] 9-phosphabicyclononyl groups. The two 9-phosphabicyclononyl groups can have both the same or each a different isomeric structure.

One or both of the phosphabicyclononyl rings is suitably substituted with one or more suitable organic groups containing carbon atoms and/or hetero-atoms. Suitable substituents include groups containing hetero-atoms such as halides, sulphur, phosphorus, oxygen and nitrogen. Examples of such groups include chloride, bromide, iodide and groups of the general formula —O—H, —O—$R^2$, —CO—$R^2$, —CO—O—$R^2$, —S—H, —S—$R^2$, —CO—S—$R^2$, —NH$_2$, —NHR$^2$, —NR$^2$R$^3$, —CO—NH$_2$, —CO—NHR$^2$, —CO—NR$^2$ R$^3$ in which $R^2$ and $R^3$, independently, represent alkyl groups having from 1 to 4 carbon atoms like methyl, ethyl, propyl, isopropyl and n-butyl.

If a phosphabicyclononyl ring is substituted, it is preferably substituted with one or more alkyl groups, preferably having from 1 to 10 carbon atoms, more preferably from 1 to 4 carbon atoms. Linear, branched or cyclic alkyl groups can be used. Suitable alkyl groups include, methyl, ethyl, propyl, iso-propyl, butyl and iso-butyl. More suitably methyl groups are used. The substituted phosphabicyclononyl ring can be mono- or poly-substituted and is preferably di-substituted. Most preferably the phosphabicyclononyl ring is substituted with two methyl groups.

Suitable bidentate ligands of formula (I) thus include for example isomers of 1,2-P,P'bis(9-phos-phabicyclononyl) propane; 2,3-P,P'bis(9-phos-phabicyclononyl)butane; 2,3-P,P'bis(9-phos-phabicyclononyl)pentane; and mixtures thereof.

These ligands can be prepared as for example described in M. D. Fryzuk et al., *J.Am. Chem. Soc.*, 1977 (Vol.99), p. 6262–6667).

Suitable sources for palladium cations of component (a) include its salts, such as for example the salts of palladium and sulphuric acid or sulphonic acids or palladium complexes, e.g. with carbon monoxide or acetylacetonate. Preferably, a salt of palladium and a carboxylic acid is used, suitably a carboxylic acid with up to 12 carbon atoms, such as salts of acetic acid, propionic acid and butanoic acid, or salts of substituted carboxylic acids such as trichloroacetic acid and trifluoroacetic acid. A very suitable source is palladium(II) acetate.

The source of anions of component (c) is preferably an acid. A wide range of acids can be used, including mineral acids, such as sulphuric acid, nitric acid and phosphoric acid, and organic acids, such as acetylacetonic acids, sulphonic acids, carboxylic acids and halogenated carboxylic acids such as trifluoroacetic acid. Preferably, a carboxylic acid is used. When a carboxylic acid, is used, preferably an acid with a pKa value>1 and more preferably an acid with a pKa in the range from 1 to 6, in aqueous solution at a temperature of 25° C. is used. Exemplary carboxylic acids are benzoic acid, acetic acid, valeric acid, butanoic acid, or nonanoic acid. Also acids corresponding with the ester (by-)products can be advantageously used in the process of the invention. The use of these acids is advantageous because they are readily obtainable by hydrolysis of these ester (by-)products. Examples of these acids are dicarboxylic acids like for example adipic acid, glutaric acid and fumaric acid; monoesters of dicarboxylic acids like for example monoalkyladipate and monoalkylmethylglutarate.

In another preferred embodiment the source of anions is a tertiary carboxylic acid, i.e. an acid with the formula (II)

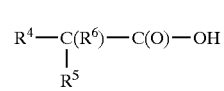

(II)

wherein $R^4$, $R^5$ and $R^6$ independently represent alkyl or aryl groups. Suitably the tertiary carboxylic acid used contains a total of from 5 to 20 carbon atoms, more preferably from 5 to 15 and most preferably from 8 to 10 carbon atoms.

Advantageously $R^4$, $R^5$ and $R^6$ are alkyl groups, preferably having from 1 to 16 carbon atoms, more preferably from 1 to 10 carbon atoms. Linear, branched or cyclic alkyl groups can be used. The alkyl groups may be substituted with aryl groups such as for example a phenyl group. Examples of suitable alkyl groups include methyl, ethyl, n-propyl, iso-propyl, n-butyl, iso-propyl, tert-butyl and n-pentyl. Preferably at least one, and more preferably two, of $R^2$, $R^3$ and $R^4$ are a methyl or ethyl group.

Suitable tertiary carboxylic acids include 2,2-dimethyl-propanoic acid (pivalic acid), 2,2dimethyl butanoic-acid, 2-methyl-2-ethyl-butanoic acid, 2,2-dimethyl-pentanoic acid, 2-methyl-2-ethyl-pentanoic acid, isomers of tertiary C-9 acid (i.e. tertiary acids containing a total of 9 carbon atoms), isomers of tertiary C-10 acid, and isomers of tertiary C-11 acid. Isomers of tertiary C-9 acid, isomers of tertiary C-10 acid, and mixtures thereof are preferred.

In the process of the invention one tertiary carboxylic acid or a mixture of tertiary carboxylic acids, having a different total number of carbon atoms and/or having different alkyl-groups, can be used.

The presence of other acids, such as for example a linear carboxylic acid as pentanoic or pentenoic acid, can have a disadvantageous effect on the catalyst activity. Therefore the tertiary carboxylic acid is preferably present in a molar ratio of at least 2:1 with regard to any other acid present, and more preferably a molar ratio of at least 5:1.

Furthermore the presence of a substoichiometric amount of halide anions is preferred, based on the amount of palladium cations. The presence of a substoichiometric amount of halide anions has a significantly favourable effect in that the conversion reaction proceeds at high rate, even at moderate temperatures. By "substoichiometric" is understood that less halide anions are present than required to neutralise the palladium cations, i.e. that the molar ratio of dissociated halide anions versus palladium cations is less than 2:1. It has surprisingly been found that when the catalyst system comprises a tertiary carboxylic acid and a substoichiometric amount of halide anions, even further improved catalyst activity can be obtained, resulting in surprisingly high reation rates.

Preferably the source of halide anions is a source of chloride, bromide or iodide anions, and more preferably a source of iodide anions is used. From a technical point of view based on its greater promoting effect the iodide anions are preferred.

Suitable sources of the halide anion include both hydrogen halides, e.g. HCl, HBr and HI, quaternary ammonium or phosphonium halides, e.g., triphenylmethylphosphonium chloride and triphenylphosphonium bromide, and metal halides e.g., NaCl, NaI, $MgBr_2$, $ZnCl_2$, $ZnI_2$, LiBr, RbCl, CsCl, CsI, $MgI_2$ and CuCl, in particular alkali or earth alkaline metal halides. A preferred source of halide anion is hydrogen iodide.

In a special preferred embodiment hydrogen iodide is used as a source of anions in combination with a tertiary carboxylic acid.

WO-A-9738964 describes a process for the carbonylation of ethylenically unsaturated compounds by reaction thereof with carbon monoxide and an alkanol in the presence a catalyst system obtainable by combining a) a source of a group VIII cation, exemplified by palladium cations; (b) a phosphine compound acting as a ligand; and (c) a source of anions, other than halide anions, carried out in the presence of substoichiometric amounts of halide anions. As preferred bidentate ligands are mentioned 1,2-P,P'-bis(9-phosphabicyclononyl)ethane and 1,3-P,P'-bis(9-phosphabicyclononyl)propane. As source of anions, preferably anions are used that are the conjugated base of acids having a pKa (measured at 18° C. in water) of less than 3, preferably less than 2. Although moderate catalyst activity is obtained, there is still room for further improvement regarding catalyst activity.

The use of pivalic acid (i.e. 2,2-dimethylpropanoic acid) as a possible source of anions is mentioned in EP-A-577204. EP-A-577204 describes a process wherein a conjugated diene is reacted with carbon monoxide and an alkanol in the presence of a catalyst system. The catalyst system includes a source of palladium, two types of bidentate diphosphine ligand and a source of anions. One type of bidentate diphospine ligand is a diphospine of formula (III)

$R^5R^6$>P—R—P<$R^7R^8$   (III)

Examples of $R^5$, $R^6$, $R^7$ and $R^8$ include pentamethylene, hexamethylene and cyclooctylene. 1,3-bis (cyclooctylenephosphino)propane (i.e. 1,3-P,P'bis(9-phosphabicyclononyl)propane) is mentioned as a preferred bidentate diphosphine ligand of this type. Further, the use of a source of halide anions as hydrogen chloride is considered disadvantageous because of its corrosive nature and the source of palladium is preferably free of halide.

The conjugated diene preferably is a conjugated diene having from 4 to 20, more preferably from 4 to 8 carbon atoms per molecule. Examples of conjugated dienes include 1,3-butadiene, 1,3 pentadiene, 1,3-hexadiene, 1,3-cyclohexadiene, 2,4-heptadiene and 2-methyl-1,3-butadiene. Aromatically delocalised double bonds are excluded from the scope of the present invention. However, the aliphatic conjugated dienes can have non-aliphatic groups, such as phenyl groups, substituted onto the —C=C—C=C— backbone. Preferably, the conjugated diene is 1,3-butadiene.

Preferred hydroxyl group containing compounds in the process of the invention are alkanols with 1 to 20, more preferably with 1 to 6 carbon atoms per molecule and alkanediols with 2–20, more preferably 2 to 6 carbon atoms per molecule. The alkanols can be aliphatic, cycloaliphatic or aromatic. Suitable alkanols in the process of the invention include methanol, ethanol, ethanediol, propanol, 1,3-propanediol, iso-propanol, butanol, iso-butanol, tert.butanol, pentanol, hexanol, cyclohexanol and phenol. Preferably methanol or ethanol is used as a hydroxyl group containing compound.

The use of these alkanols or alkanediols as a hydroxyl group containing compound in the carboxylation process of 1,3-butadiene and derivatives thereof enables the production of alkyl pentenoates and alkyl adipates and derivatives thereof of which the alkyl group contains 1 to 20, more preferably 1 to 6 carbon atoms.

Methanol is especially preferred as a hydroxyl group containing compound. The use of methanol as a hydroxyl group containing compound in the carbonylation process of 1,3-butadiene enables the production of methyl-pentenoate and/or dimethyl adipate. Dimethyl adipate is an intermediate compound in the preparation of adipic acid, an intermediate compound to prepare Nylon 6,6. Methyl-pentenoate is an important intermediate in the production process of ε-caprolactam. For the preparation of ε-caprolactam, methyl-pentenoate is hydroformylated to methyl formylvalerate, which after reductive amination and cyclisation forms ε-caprolactam. ε-Caprolactam is a starting material in the manufacture of Nylon 6 fibres or engineering plastics. Hydroformylation, reductive amination and cyclisation can be performed in any manner known to a person skilled in the art. Suitable processes are described in WO-A-9733854, WO-A-9835938 and WO-A-9837063.

In the process of the invention liquid carbonylation product and/or surplus of a carbonylation reactant such as conjugated diene or hydroxyl group containing compound will serve as solvent during the reaction. It is also possible to perform the reaction in the presence of an extra inert solvent. Suitable extra inert solvents are for example aprotic compounds. Examples include saturated hydrocarbons, such as for example paraffins and isoalkanes; ketones, such as for example methylbutylketone; ethers, such as for example anisole, 2,5,8-trioxanonane (diglyme), diethylether, tetrahydrofuran, diphenylether, diisopropylether and the dimethylether of diethyleneglycol; esters, such as for example methylacetaat, dimethyladipate and butyrolactone; amides, such as for example dimethylacetamide and N-methylpyrrolidone; and sulphones, such as for example diisopropylsulphone, sulfolane, 2-methylsulfolane and 2-methyl-4-ethylsulfolane.

The carbonylation is suitably carried out at moderate reaction conditions. Hence temperatures in the range of 20 to 200° C. are recommended, preferred temperatures being in the range of 70 to 160° C.

Carbon monoxide pressures in the range of 0.1–6.5 MPa are preferred. In the process according to the present invention, the carbon monoxide can be used in its pure form or diluted with an inert gas such as nitrogen, carbon dioxide or noble gases such as argon. Small amounts of hydrogen can also be present. In general, the presence of more than 5% hydrogen is undesirable, since this can cause hydrogenation of the conjugated diene.

The molar ratio of hydroxyl group containing compound to conjugated dienes, in particular butadiene, can vary between wide limits and suitably lies in the range of 0.1:1 to 10:1, more suitably from 1:1 to 6:1. Generally a molar ratio near the higher limit of this range favours the preparation of diesters and a molar ratio near the lower limit of this range favours the preparation of mono-esters.

The palladium concentration in the reaction mixture is preferably as high as possible because the rate of reaction per unit of reactor volume will be higher. The upper limit will normally be determined by the solubility of palladium in the reaction mixture. The upper limit can be determined by one skilled in the art. Preferably, the amount of palladium is between 400 and 4000 ppm and more preferably between 800 and 1200 ppm.

The ratio of moles of bidentate ligand, i.e. catalyst component (b), per mole atom of palladium, i.e. catalyst component (a), ranges from 0.5 to 10, preferably from 1 to 2. When this ratio is lower than 1 palladium can precipitate, whereas when this ratio is higher than 10, excessive ligand consumption can occur. It has been found that the process of the invention is preferably carried out with a slight molar excess of ligand to palladium because the ligand degradation is decreased or even no ligand degradation occurs. Most preferably, the bidentate ligand/palladium molar ratio is higher than 1.05 and less than 1.2. When performing the process of the invention with a slight excess of ligand to palladium, it will be preferred to monitor the concentration (and degradation) of the ligand during the course of the process and add fresh ligand in order to remain in the preferred ranges of operation.

The quantity of, for instance in-situ prepared, carboxylic acid used in the carbonylation reaction can vary within wide ranges. The amount of acid preferably ranges between 0.1 and 40 wt. %, more preferably between 0.5–10 wt. % and most preferably between 1 to 8 wt. % (based on the total reactor mixture). Preferably, the amount of acid ranges from 0.1 mole to 1000 mole of acid per mole of palladium cation. If halide anions are present, the molar ratio of dissociated halide anions versus palladium cations is preferably in the range from 0.001:1 up to 1.5:1, more preferably in the range from 0.001:1 to 0.5:1.

The process of the present invention can be used for each range of mole conjugated diene per mole atom of palladium. Conveniently, the amount of catalyst system is small. The ratio of mole conjugated diene per mole of palladium cation can vary between wide limits, suitably in the range from $1 \times 10^1$ to $2 \times 10^7$ mole conjugated diene per mole of palladium cation, dependent on whether a continuous, semi-continuous or batch-wise process is being used. The use of a continuous manner of operation conveniently allows for high molar ratios near the upper limit of this range, e.g. in the range from $2 \times 10^3$ to $2 \times 10^7$. For a batch-wise process, suitably the ratio of mole conjugated diene per mole of palladium cation is in the range of $2 \times 10^2$ to $2 \times 10^6$ more suitably in the range of $2 \times 10^2$ to $2 \times 10^5$.

Some of the catalyst systems described herein are novel. The invention therefore further provides a catalyst system comprising:

(a) a source of palladium cations;

(b) a bidentate diphospine ligand having the general formula I $$X^1\text{—}R\text{—}X^2 \quad\quad (I)$$

wherein $X^1$ and $X^2$ represent a cyclic group with at least 5 ring atoms, of which one is a phosphorus atom, and R represents a bivalent organic bridging group, connecting both phosphorus atoms, preferably substituted with at least one substituent;

(c) a source of anions derived from a tertiary carboxylic acid of the formula (II)

wherein $R^4$, $R^5$ and $R^6$ independently represent alkyl or aryl groups; and (d) a substoichiometric amount of halide anions; with the proviso that the catalyst system contains less than 0.5 mole of an anion, other than halide anions, that is the conjugated base of an acid having a pKa less than 3, per mole palladium cations.

Preferences for this catalyst system are as described hereinbefore for the process.

The invention will be illustrated by the following examples.

COMPARATIVE EXPERIMENT A

A 300 ml magnetically stirred HASTELLOY C autoclave (HASTELLOY is a registered trademark) was filled with 10 ml methanol, 30 ml dimethyladipate, 1.0 mmol palladium acetate, 1.5 mmol 1,2-P,P'bis(9-phosphabicyclononyl) ethane and 10 mmol pivalic acid. Subsequently the autoclave was closed, evacuated and hereafter 20 ml (circa 230 mmol) of 1,3butadiene was added, and carbon monoxide to an initial carbon monoxide pressure of 4 MPa was added. The autoclave was heated to 135° C. After a residence time of about 2 hours, the contents of the autoclave were analysed by means of gas-liquid chromatography. The initial rate of carbonylation was 120 mol CO/grams atom palladium/hour and is calculated from the mean rate of carbon monoxide consumption over the first 30% butadiene conversion. After about 2 hours 90% of the 1,3-butadiene was converted. The product consisted mainly of esters. 95% of the esters formed are mono-esters. The formed mono-esters consist of 91% methyl-3-pentenoate, 8% methyl-2-pentenoate and 1% methyl-4-pentenoate.

EXAMPLE 1

Comparative example A was repeated, except that instead of 1.5 mmol 1,2-P,P'bis(9-phosphabicyclononyl)ethane, 1.5 mmol R,S meso 2,3-P,P'bis(9-phosphabicyclononyl)butane was used as ligand. The initial rate of carbonylation was 265 mol CO/grams atom palladium/hour. After about 2 hours 95% of the 1,3-butadiene was converted. The product consisted mainly of esters. More than 95% of the esters formed are mono-esters. The formed monoesters consist of 98% methyl-3-pentenoate, 1.5% methyl-2-pentenoate and less than 1% methyl-4-pentenoate.

EXAMPLE 2

Example 1 was repeated, except that 0.1 mmol HI was added. Due to exothermic effects, the reaction temperature increased to 145° C. The initial rate of carbonylation was 750 mol CO/grams atom palladium/hour.

After about 2 hours 100% of the 1,3-butadiene was converted. The product consisted mainly of esters. About 95% of the esters formed are monoesters. The formed monoesters consist of 97% methyl-3pentenoate, 2.5% methyl-2-pentenoate and less than 1% methyl-4-pentenoate.

EXAMPLE 3

Example 2 was repeated, except that instead 1.5 mmol R,S-meso-2,3-P,P'bis(9-phosphabicyclononyl)butane, 0.33 mmol R,S-meso-2,3-P,P'bis(9-phosphabicyclononyl)butane was used and instead of 1.0 mmol palladium acetate, 0.25 mmol palladium acetate was used. The initial rate of carbonylation was 560 mol CO/grams atom palladium/hour. After about 2 hours more than 95% of the 1,3-butadiene was converted. The product consisted mainly of esters. More than 95% of the esters formed are mono-esters. The formed monoesters consist of 98% methyl-3-pentenoate, 1.5% methyl-2-pentenoate and less than 1% methyl-4pentenoate.

EXAMPLE 4

Example 3 was repeated, except that instead of 10 mmol pivalic acid, 10 mmol of an mixture of isomers of C-10 tertiary carboxylic acids (ex. Shell, sold under the trademark VERSATIC-10) was used. The initial rate of carbonylation was 560 mol CO/grams atom palladium/hour. The product consisted mainly of esters. After about 2 hours more than 95% of the 1,3-butadiene was converted. More than 95% of the esters formed are mono-esters. The formed mono-esters consist of 98% methyl-3-pentenoate, 1.5% methyl-2-pentenoate and less than 1% methyl-4-pentenoate.

EXAMPLE 5

Example 3 was repeated, except that instead of 0.33 mmol R,S-meso-2,3-P,P'bis(9-phosphabicyclononyl)butane, 0.33 mmol 1,2-P,P'bis(9-phosphabicyclononyl)benzene was used. The initial rate of carbonylation was 400 mol CO/grams atom palladium/hour. After about 2 hours about 90% of the 1,3-butadiene was converted. The product consisted mainly of esters. More than 95% of the esters formed are mono-esters. The formed mono-esters consist of 98% methyl-3-pentenoate, 1.5% methyl-2-pentenoate and less than 1% methyl-4-pentenoate.

EXAMPLE 6

Example 5 was repeated, except that the autoclave was heated to only 110° C. instead of to 135° C. and residence time was about 4 hours instead of about 2 hours. The initial rate of carbonylation was 260 mol CO/grams atom palladium/hour. After about 4 hours about 90% of the 1,3-butadiene was converted. The product consisted mainly of esters. More than 95% of the esters formed are mono-esters. The formed mono-esters consist of 99% methyl-3-pentenoate, less than 1% methyl-2-pentenoate and less than 1% methyl-4-pentenoate.

From the results of examples 1–6 and comparative experiment A it can be concluded that surprisingly the use of substituted (on the bridge) diphosphine ligands renders the catalyst system much more active than the use of non-substituted (on the bridge) diphosphine ligands. As illustrated by comparing comparative experiment A with examples 1–6, the initial rate of carbonylation can be more than doubled and in addition a higher selectivity to carbonylation is obtained.

EXAMPLES 7–10 AND COMPARATIVE EXPERIMENTS B–D

A 300 ml magnetically stirred Hastelloy C autoclave (Hastelloy is a registered trademark) was filled with 10 ml methanol, an amount of solvent as indicated in table I, an amount of palladium acetate as indicated in table I, an amount of a specific bidentate phosphine ligand as indicated in table I, an amount of specific acid as indicated in table I, and optionally an amount of source of halide anions as indicated in table I. Subsequently the autoclave was closed, evacuated and hereafter 20 ml (circa 230 mmol) of 1,3-butadiene was added, and carbon monoxide to an initial carbon monoxide pressure of 4 MPa was added. The autoclave was heated to 135° C. After a residence time of about 2 hours, the autoclave was cooled and the contents of the autoclave were analyzed by means of gas-liquid chromatography. The initial rate of carbonylation is indicated in table I. The initial rate of carbonylation is expressed in mol CO/grams atom palladium/hour and is defined as the mean rate of carbon monoxide consumption over the first 30% butadiene conversion.

The results of each example are summarized in Table I. From the results of the examples it can be concluded that surprisingly the use of a substituted (on the bridge) diphosphine ligand in combination with a tertiary carboxylic acid and a source of halide anions renders the catalyst system much more active compared with the use of a non-substituted (on the bridge) diphosphine ligand in combination with only a tertiary carboxylic acid or only a source of halide anions. As illustrated by comparing comparative experiments B–D with examples 7–10, the initial rate of carbonylation can be more than doubled.

In table I, the following abbreviations are used:

PBCE=1,2-P,P'bis(9-phosphabicyclononyl)ethane

PBCP=1,2-P,P'bis(9-phosphabicyclononyl)propane

PBCB=R,S-meso-2,3-P,P'bis(9-phosphabicyclononyl)-butane

HI=hydrogen iodide

VERSATIC-10=mixture of isomers of C-10 tertiary carboxylic acid obtained from Shell (VERSATIC is a trademark).

TABLE I

Carbonylation of butadiene

| Example | Amount of Pd(Ac)$_2$ (mmol) | Bidentate diphosphine ligand (mmol) | acid (mmol) | source of halide anions (mmol) | Solvent (ml) | reaction rate (mol/mol/hour) |
|---|---|---|---|---|---|---|
| B | 1 | PBCE 1.5 | pivalic acid 10 | — | dimethyl adipate 30 | 100 |
| C | 1 | PBCE 1.5 | pivalic acid 10 | — | anisole 30 | 140 |
| D | 1 | PBCE 1.5 | pentenoic acid 10 | HI 0.1 | dimethyl adipate 30 | 120 |
| 7 | 1 | PBCB 1.5 | pivalic acid 10 | HI 0.1 | dimethyl adipate 30 | 750* |
| 8 | 0.25 | PBCB 0.33 | pivalic acid 10 | HI 0.1 | dimethyl adipate 30 | 560 |

TABLE I-continued

Carbonylation of butadiene

| Example | Amount of Pd(Ac)$_2$ (mmol) | Bidentate diphosphine ligand (mmol) | acid (mmol) | source of halide anions (mmol) | Solvent (ml) | reaction rate (mol/mol/hour) |
|---|---|---|---|---|---|---|
| 9 | 0.25 | PBCP 0.33 | pivalic acid 10 | HI 0.1 | dimethyl adipate 30 | 400 |
| 10 | 0.25 | PBCB 0.33 | VERSATIC-10 10 | HI 0.1 | dimethyl adipate 30 | 560 |

*Due to exothermic effects, the reaction temperature during this experiment increased to 145° C.

What is claimed is:

1. Process for the carbonylation of a conjugated diene by reacting the conjugated diene with carbon monoxide and an hydroxyl group containing compound in the presence of a catalyst system comprising:
   (a) a source of palladium cations,
   (b) a diphosphine ligand, and
   (c) a source of anions, wherein the diphosphine ligand is a ligand having the general formula I $$X^1\text{---}R\text{---}X^2 \quad (I)$$

wherein $X^1$ and $X^2$ represent a cyclic group with at least 5 ring atoms, of which one is a phosphorus atom, and R represents a bivalent aliphatic bridging group, connecting both phosphorus atoms, containing from 2 to 4 atoms in the bridge, which is substituted with at least one substituent or R represents a phenyl group with both phosphorus groups bound to the 1,2-position.

2. A process as claimed in claim 1, wherein R represents a bivalent aliphatic bridging group, connecting both phosphorus atoms, containing from 2 to 4 atoms in the bridge, which is substituted with at least two alkyl groups.

3. A process as claimed in claim 1, wherein the bridging group is a substituted dimethylene or trimethylene group.

4. A process as claimed in claim 1, wherein the carbon-atoms of the bridge, which are connected with the phosphorus atoms, are substituted with alkyl groups.

5. A process as claimed in claim 1, wherein the bridging group R is di-substituted in the bridge with two methyl groups.

6. A process as claimed in claim 1, wherein both $X^1$ and $X^2$ represent a substituted or non-substituted 9-phosphabicyclononyl group.

7. A process as claimed in claim 1, wherein the conjugated diene is 1,3-butadiene.

8. A process as claimed in claim 1, wherein the hydroxyl group containing compound is an alkanol with 1 to 20 carbon atoms per molecule or an alkanediol with 2 to 20 carbon atoms per molecule.

9. A process as claimed in claim 1, wherein a substoichiometric amount of halide anions is present, based on the amount of palladium cations.

10. A process as claimed in claim 9, wherein the source of halide anions is a source of iodide anions.

11. A process as claimed in claim 10, wherein the source of halide anions is hydrogen iodide.

12. A process as claimed in claim 9, wherein the molar ratio of halide anions versus palladium cations is in the range from 0.001:1 up to 1.5:1.

13. A process as claimed in claim 1, wherein the source of anions is derived from a tertiary carboxylic acid with formula (II)

wherein $R^4$, $R^5$ and $R^6$ independently represent alkyl or aryl groups.

14. A process as claimed in claim 13, wherein at least one of $R^4$, $R^5$ and $R^6$ is a methyl or ethyl group.

15. Catalyst system comprising
   (a) a source of palladium cations;
   (b) a bidentate diphospine ligand having the general formula I $$X^1\text{---}R\text{---}X^2 \quad (I)$$

wherein $X^1$ and $X^2$ represent a cyclic group with at least 5 ring atoms, of which one is a phosphorus atom, and R represents a bivalent organic bridging group, connecting both phosphorus atoms;
   (c) a source of anions derived from a tertiary carboxylic acid of the formula (II)

wherein $R^4$, $R^5$ and $R^6$ independently represent alkyl or aryl groups; and
   (d) a substoichiometric amount of halide anions; with the proviso that the catalyst system contains less than 0.5 mole of an anion, other than halide anions, that is the conjugated base of an acid having a pKa less than 3, per mole palladium cations.

16. Catalyst system as claimed in claim 15, wherein the bridging group R is substituted with at least one substituent.

* * * * *

UNITED STATES PATENT AND TRADEMARK OFFICE
CERTIFICATE OF CORRECTION

PATENT NO. : 6,835,850 B2
DATED : December 28, 2004
INVENTOR(S) : Drent et al.

It is certified that error appears in the above-identified patent and that said Letters Patent is hereby corrected as shown below:

<u>Title page,</u>
Item [73], Assignee, change "DSW" to -- DSM --

Signed and Sealed this

Twelfth Day of July, 2005

JON W. DUDAS
*Director of the United States Patent and Trademark Office*